(12) United States Patent
O'Halloran et al.

(10) Patent No.: US 11,850,593 B2
(45) Date of Patent: Dec. 26, 2023

(54) TARGET CELL CONCENTRATION USING DIELECTROPHORESIS (DEP)

(71) Applicant: QUANTUMDX GROUP LIMITED, Newcastle Upon Tyne (GB)

(72) Inventors: Jonathan O'Halloran, Newcastle Upon Tyne (GB); Heather Murton, Newcastle Upon Tyne (GB); Stephen Osborne, Newcastle Upon Tyne (GB); Eduardo Boada, Newcastle Upon Tyne (GB); Jonathan Salmon, Newcastle Upon Tyne (GB)

(73) Assignee: QUANTUMDX GROUP LIMITED, Newcastle Upon Tyne (GB)

( * ) Notice: Subject to any disclaimer, the term of this patent is extended or adjusted under 35 U.S.C. 154(b) by 867 days.

(21) Appl. No.: 16/900,703

(22) Filed: Jun. 12, 2020

(65) Prior Publication Data
US 2020/0298235 A1     Sep. 24, 2020

Related U.S. Application Data

(63) Continuation of application No. 16/311,147, filed as application No. PCT/EP2017/065019 on Jun. 20, 2017, now Pat. No. 10,710,075.

(30) Foreign Application Priority Data

Jun. 21, 2016  (GB) ..................... 1610830
May 11, 2017  (GB) ..................... 1707566

(51) Int. Cl.
*B01L 3/00*     (2006.01)
*G01N 33/569*   (2006.01)

(52) U.S. Cl.
CPC .. *B01L 3/502761* (2013.01); *G01N 33/56966* (2013.01); *B01L 2200/0631* (2013.01);
(Continued)

(58) Field of Classification Search
None
See application file for complete search history.

(56) References Cited

U.S. PATENT DOCUMENTS

2005/0196855 A1  9/2005  Gau
2010/0075311 A1  3/2010  Barrault
(Continued)

FOREIGN PATENT DOCUMENTS

| JP | 2015-534810 A | 12/2015 |
| WO | WO 2010/080978 A2 | 7/2010 |
| WO | WO 2014/207618 A1 | 12/2014 |

OTHER PUBLICATIONS

Bhattacharya, S., et al., PCR-based detection in a micro-fabricated platform, Lab on a Chip, Royal Society of Chemistry, vol. 8, No. 7, pp. 1130-1136, 2008.
(Continued)

*Primary Examiner* — Lyle Alexander
*Assistant Examiner* — Bryan Kilpatrick
(74) *Attorney, Agent, or Firm* — Knobbe, Martens, Olson & Bear LLP

(57) ABSTRACT

Methods and devices for concentrating target cells using dielectrophoresis (DEP) are disclosed. The method allows relatively high throughput of sample through a microfluidic device in order to allow rapid capture of target cells even when they are present in low concentrations within the sample. The method utilizes multiple chambers through which samples will flow, the chambers arranged such that the first capture area has a larger area and faster flow rate than a second chamber, the second chamber being positioned downstream of the first capture area and being smaller with a slower flow rate to further concentrate the material captured in the first capture area.

15 Claims, 4 Drawing Sheets

(52) U.S. Cl.
CPC ............... *B01L 2200/0668* (2013.01); *B01L 2300/0645* (2013.01); *B01L 2300/0816* (2013.01); *B01L 2300/0864* (2013.01); *B01L 2300/0867* (2013.01); *B01L 2400/0424* (2013.01)

(56) References Cited

U.S. PATENT DOCUMENTS

| | | | |
|---|---|---|---|
| 2010/0267162 A1 | 10/2010 | Kartalov | |
| 2014/0116881 A1 | 5/2014 | Chapman | |
| 2015/0193928 A1* | 7/2015 | Bharadwaj | H04N 7/18 382/134 |

OTHER PUBLICATIONS

International Preliminary Report on Patentability, dated Aug. 13, 2018, in International Application No. PCT/EP2017/065019.
International Search Report and Written Opinion, dated Sep. 18, 2017, in International Application No. PCT/EP2017/065019.
Notification of Reasons for Refusal, dated Jun. 4, 2019, in Japanese Application No. 2018-566214.

* cited by examiner

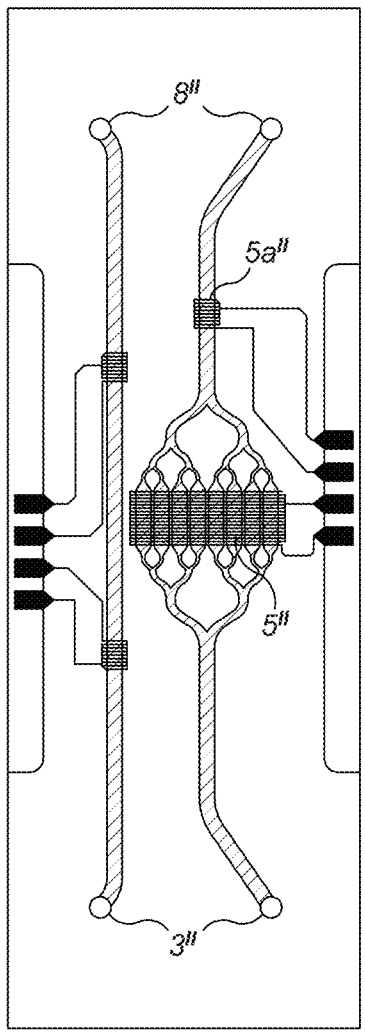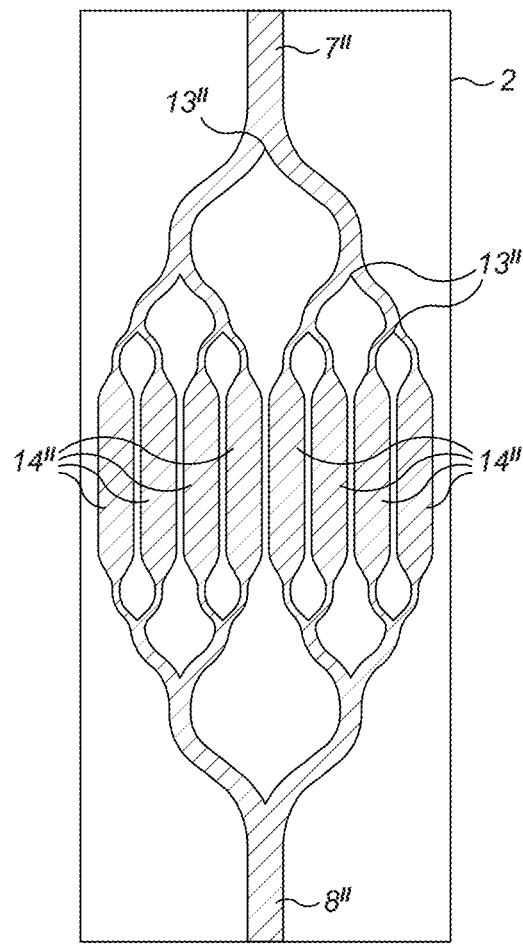
FIG. 3a
FIG. 3b

TARGET CELL CONCENTRATION USING DIELECTROPHORESIS (DEP)

PRIORITY AND CROSS REFERENCE TO RELATED APPLICATIONS

This application is a Continuation Application of U.S. application Ser. No. 16/311,147, filed Dec. 18, 2018, which is the U.S. National Phase Application under 35 U.S.C. § 371 of International Application No. PCT/EP2017/065019, filed Jun. 20, 2017, designating the U.S. and published in English as WO 2017/220534 A1 on Dec. 28, 2017, which claims the benefit of GB Application No. GB 1610830.0, filed Jun. 21, 2016, and GB Application No. GB 1707566.4, filed May 11, 2017. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to methods of and devices for concentrating target cells using dielectrophoresis (DEP).

SUMMARY

The present invention relates to methods of and devices for concentrating target cells using dielectrophoresis (DEP). In particular, the method allows relatively high throughput of sample (preferably using sample volumes of up to 100 ml, or up to 10 ml, or up to 1 ml) through a microfluidic device in order to allow rapid capture of target cells even when they are present in low concentrations within the sample. The method utilises multiple areas or chambers through which samples will flow, the areas or chambers arranged such that the first capture area has a larger area and faster flow rate than a second chamber, the second chamber being positioned downstream of the first capture area and being smaller with a slower flow rate to further concentrate the material captured in the first capture area.

BRIEF DESCRIPTION OF THE DRAWINGS

In order to provide a better understanding of the present invention, embodiments will be described, by way of example only, and with reference to the following drawings;

FIG. 3a shows an alternative embodiment of a device according to the present invention with FIG. 3b showing a larger view of the first capture area in said device which includes bifurcated channels in accordance with the present invention.

DETAILED DESCRIPTION

Figure 1:
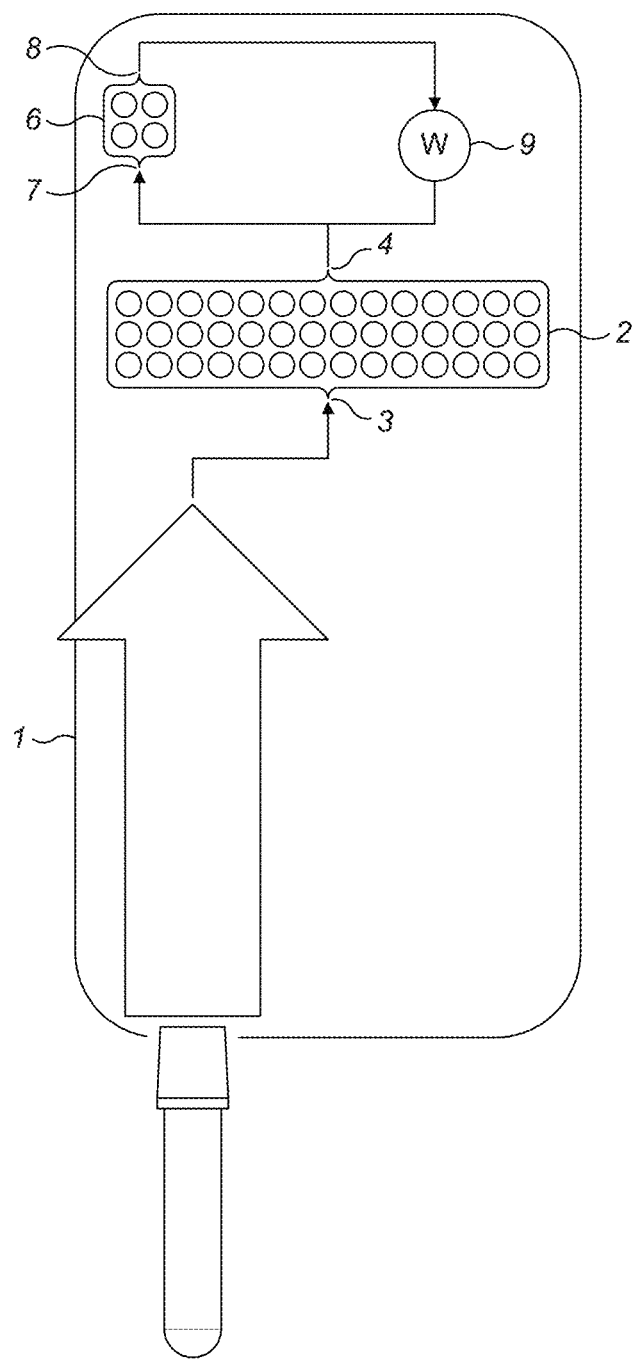
FIG. 1 shows an embodiment of a microfluidic device, or portion thereof, in accordance with an embodiment of the present invention.

Early detection of pathogens is key to effective and timely treatment in many cases. For example, Tuberculosis (TB) causes 2 million deaths per year, despite most cases being curable. With no effective vaccine available, early diagnosis and effective treatment are crucial to eliminating this disease. An estimated 60% of patients requiring a TB test present in local community-based health centres, however diagnostic testing for multi-drug resistant tuberculosis (MDR-TB) requires expensive and complex laboratory equipment and highly skilled staff found in referral or satellite laboratories. Results, including a panel of drug resistance markers, may not be returned for weeks during which time the infection can spread within the community.

Advances in microfluidics are such that point of care (POC) diagnostic devices are moving closer to becoming a reality. However, there are still significant bottlenecks in the proposed POC systems, many of which relate to the pre-processing of samples for testing where samples with potentially low concentrations of pathogens must be processed to provide more concentrated volumes of pathogenic material. There are also challenges in processing relatively large volumes of sample in acceptable timeframes to be truly suitable for the provision of a point of care diagnosis.

Dielectrophoresis (DEP) is where a force is exerted on a dielectric or polarisable particle, causing it to move, when it is subjected to a spatially non-uniform electric field. DEP motion can be induced toward an electrode surface (positive DEP) or away from an electrode surface (negative DEP).

DEP can be used for microfluidic continuous flow processing of a sample potentially containing target cells to concentrate the target cells. A DEP electrode is tuned to selectively trap target cells suspended in a sample stream onto the designated area inside a microfluidic channel, whilst unwanted cells and material continue to be drawn through the microfluidic channel by the flow. This requires target specific DEP forces that are strong enough to continuously trap the cells against the hydrodynamic forces. DEP operation is effective for the trapping based cell separation and concentration because the target cells can be captured on the electrode's surfaces and can then be released by turning off the electric field.

Whilst such an approach can be useful, it is currently limited in a clinical setting due to the speed of processing. Particularly in cases where the pathogen or target cell may be present only at very low concentrations in a sample, relatively high volumes of sample need to be flowed through the microfluidics system. If the sample is flowed through a typical DEP microfluidic system at too high a flow rate the efficiency of capture of target cells is reduced—without wishing to be limited by theory it is believed that the high flow rate is detrimental for the following reasons (i) some cells escape capture, as those further from the electrodes are subject to less force and therefore may be overcome by the hydrodynamic forces, (ii) that over time it effectively washes off previously trapped cells. Therefore DEP capture would need to be run slowly, adding significant time to the overall POC diagnostic process.

An example of a device that has limitations on flow can be seen in Shantanu Bhattacharya et al; PCR-based detection in a microfabricated platform; Lab On A Chip Vol 8; 1 Jan. 2008; p 1130-1136, which is hereby incorporated by reference in its entirety.

The present invention aims to obviate or mitigate one or more of the drawbacks associated with the prior art.

In accordance with a first aspect of the present invention there is provided a method for concentrating target particles in a sample, comprising the steps of; providing a microfluidic device, said device comprising;

at least one first capture area comprising a plurality of electrodes which when activated trap target particles at their surface, for selectively and releasably capturing target particles, such plurality of electrodes arranged such that a sample flowing through the first capture area will flow over said plurality of electrodes, and at least one inlet, wherein the at least one inlet is divided into multiple channels, where each channel is of smaller circumference than the at least one inlet;

a second area downstream of the first capture area and in fluid communication therewith, the second area being of smaller volume than the first capture area and comprising, a second plurality of electrodes (5a, 5a', 5a"), which, when activated, trap target particles at their surface arranged such that a sample flowing through the second area will flow over the second plurality of electrodes; introducing a sample into the first capture area and flowing the sample through the first capture area at a first flow rate, and with the first plurality of electrodes able to trap any target particles;

releasing trapped target particles from the first plurality of electrodes to provide an enriched sample;

introducing the enriched sample to the second area and flowing the enriched sample through the second area at a second flow rate which is lower than the first flow rate, and with the second plurality of electrodes arranged to trap target particles;

carrying out further processing steps.

Preferably the target particles are target cells.

Preferably the means for selectively and releasably capturing target cells is a plurality of electrodes, which, when activated, trap target cells at their surface.

Preferably the second means capture target cells is a plurality of electrodes which, when activated, trap target cells at their surface.

Surprisingly, the inventors have found that by flowing a sample through a first larger area, such as a chamber, chamber with DEP electrodes at a relatively high flow rate allows an initial quick capture, the captured cells can then be released which can then be followed by flowing the resulting enriched flow through a second smaller chamber at a lower flow rate than in the first capture area. This allows target cell to be concentrated efficiently and quickly (particularly as compared to the method of simply flowing through a channel with a DEP electrode). In particular this allows a relatively large sample volume to be processed in a time effective manner irrespective of whether there are high or low amounts of target present. Effectively the system allows for sample to flow with a higher mean velocity across the first area than the second area.

Preferably the step of introducing a sample into the first capture area and flowing the sample through the first capture area at a first volumetric flow rate across said area, and with the first means for selectively and releasably capturing target cells able to trap any target cells, comprises introducing a sample into the first capture area and flowing the sample through the first capture area at a first flow rate, with the electrodes activated to trap any target cells. The electrodes are arranged to utilize DEP to selectively trap target cells.

Preferably the step of releasing trapped target cells from the first means for selectively and releasably capturing target cells to provide an enriched sample comprises deactivating the electrodes in the first capture area after a period of time to release trapped target cells to provide an enriched sample.

Preferably the step of introducing the enriched sample to the second chamber and flowing the enriched sample through the second chamber at a second volumetric flow rate across the second area which is lower than the first flow rate, and with the second means to capture target cells able to trap target cells comprises introducing the enriched sample to the second chamber and flowing the enriched sample through the second chamber at a second flow rate which is lower than the first flow rate, and with the electrodes activated to trap target cells. The electrodes are arranged to utilize DEP to selectively trap target cells.

Preferably the at least one first capture area comprises at least one inlet and at least one outlet.

Preferably, the second area comprises at least one inlet and at least one outlet. However the inlet an outlet may simply be formed from an area in a channel.

It will be understood that references to an enriched sample or further enriched sample will only include target cells in that case that such cells are present in the original sample i.e. if the sample contains pathogen.

Optionally the first capture area is a chamber.

Optionally the second area is a chamber.

Preferably, the at least one inlet of the first capture area is divided into multiple channels, where each channel is of smaller circumference than the at least one inlet of the first capture area.

Preferably the multiple channels are multiple parallel channels.

Advantageously, by dividing the first capture area into a plurality of, preferably parallel, smaller circumference channels this allows a relatively large volume of sample to be flowed with the characteristics of smaller volumes. As the first capture area is now effectively a capture area with plurality of channels the problems often associated with laminar flow characteristics where the center of the flow is typically faster than the edges is lessened. In particular problems associated with flow at the edges of the channels are mitigated and there are less issues with voltage drop across the electrodes.

Preferably the multiple channels rejoin at the outlet of the at least one first capture area.

Preferably the at least one inlet of the first capture area is provided with at least one bifurcation to divide it into multiple channels.

Preferably the at least one outlet of the first capture area is provided with at least one bifurcation to rejoin it into a single channels.

Advantageously using bifurcations to split the inlet channels or rejoin the outlet channels provides a reproducible and manageable way to step up or step down the pressure.

Optionally, the microfluidic device may comprise a plurality of separable portions.

Optionally, prior to deactivating the electrodes in the first capture area a new buffer or media is flowed into the first capture area. This new buffer could be water. When the electrodes are then deactivated the target cells are released into the new buffer to give an enriched sample with a higher concentration of target cells.

Preferably the sample is low salt or low ionic strength.

Optionally, further processing steps may include deactivating the electrodes in the second chamber after a period of time to release trapped target cells to provide a further enriched sample. Optionally, prior to deactivating the electrodes in the second chamber a new buffer or media is flowed into the first capture area. This new buffer could be water. When the electrodes are then deactivated the target cells are released into the new buffer to give a further enriched sample with a higher concentration of target cells.

Optionally, further processing steps may include lysing the cells in situ and optionally carrying out nucleic acid extraction and/or amplification.

Optionally, antibodies to the target cells may be introduced into the first capture area and/or the second chamber. Said antibodies may include fluorophores.

Optionally, a biological stain specific to the target cells may be introduced into the first capture area and/or the second chamber.

Optionally an optical detection device is provided.

Preferably said optical detection device is arranged to detect signals from the second chamber. Preferably said optical detection device is capable of detecting, and preferably differentiating or analysing, fluorescence. Optionally the optical detection device comprises an excitation source and a detector.

Optionally the device is provided with flow regulators. Optionally the flow regulators are pumps. Flow can be regulated in a number of ways as would be readily understood by one skilled in the art. Changes in flow can be achieved by changing the contours and sizes of the microfluidic channels and chambers and/or using additional means such as pumps.

Preferably, when the electrodes in the first capture area are activated, the sample flows out of the capture area to a waste reservoir. Preferably, when the electrodes in the first capture area are deactivated, the sample flows out of the first capture area to the second chamber.

Preferably, when the electrodes in the second chamber are activated, the sample flows out of the second chamber to a waste reservoir.

According to a second aspect of the present invention there is provided a microfluidic device for concentrating target particles, such as target cells, in a sample, comprising;
  a first capture area, the first capture area comprising a first plurality of electrodes which, when activated, trap target cells at their surface for selectively and releasably capturing target particles, said first plurality of electrodes arranged such that a sample flowing through the first capture area will flow over said first plurality of electrodes, and at least one inlet wherein said inlet is divided into multiple channels, where each channel is of smaller circumference than the at least one inlet of the first capture area;
  a second area, downstream of the first capture area and in fluid communication therewith, the second area being of smaller volume than the first capture area and comprising a second plurality of electrodes which, when activated, trap target cells at their surface to capture target particles arranged such that a sample flowing through the second area will flow over said second plurality of electrodes;
  a control module which controls the activation and deactivation of the electrodes;
  flow control means to allow flow rate through the second chamber to be lower than the flow rate through the first capture area.

Preferably the multiple channels are multiple parallel channels.

Preferably the multiple channels rejoin at the outlet of the at least one first capture area.

Preferably the at least one inlet of the first capture area is provided with at least one bifurcation to divide it into multiple channels.

Preferably the at least one outlet of the first capture area is provided with at least one bifurcation to rejoin it into a single channels.

Optionally, the microfluidic device may comprise a plurality of separable portions.

Optionally, the device comprises a new buffer or media reservoir in fluid communication with the first capture area. Optionally the new buffer or media reservoir is in fluid communication with the second chamber. Alternatively a second new buffer or media reservoir is in fluid communication with the second chamber. Optionally the new buffer or media is water. The device may further comprise a control module that introduces flow of new buffer or media into the first capture area and/or second chamber when the electrodes are deactivated.

Optionally, the device comprises a reservoir of antibodies to the target cells. Optionally the reservoir of antibodies is in fluid communication Optionally, a biological stain specific to the target cells may be introduced into the first capture area and/or the second chamber.

Optionally an optical detection device is provided.

Preferably said optical detection device is arranged to detect signals from the second chamber. Preferably said optical detection device is capable of detecting, and preferably differentiating or analysing, fluorescence. Optionally the optical detection device comprises an excitation source and a detector.

Optionally the device comprises pre-processing modules. This may include additional chambers in fluid communication with the first capture area to pre-process the sample. This could include altering the viscosity of the sample, salt content etc.

Optionally the device is provided with flow regulators. Optionally the flow regulators are pumps.

Preferably the device is provided with a waste reservoir. Optionally the waste reservoir is in fluid communication with the first capture area. Preferably the waste reservoir is in fluid communication with the second chamber.

A preferred variant of the first aspect of the invention is a method for concentrating target cells, comprising the steps of;
  providing a microfluidic device, said device comprising;
  a first capture area, the first capture area comprising a plurality of electrodes which, when activated, trap target cells at their surface, said electrodes arranged such that a sample flowing through the first capture area will flow over them;
  a second capture area downstream of the first capture area and in fluid communication therewith, the second capture area being of smaller volume than the first capture area and comprising a plurality of electrodes which, when activated, trap target cells at their surface, said electrodes arranged such that a sample flowing through the first capture area will flow over them;
  introducing a sample into the first capture area and flowing the sample through the first capture area at a first flow rate, and with the electrodes activated to trap any target cells;
  deactivating the electrodes in the first capture area after a period of time to release trapped target cells to provide an enriched sample;
  introducing the enriched sample to the second chamber and flowing the enriched sample through the second capture area at a second flow rate which is lower than the first flow rate, and with the electrodes activated to trap target cells.

A microfluidic device 1 (or portion thereof) is generally depicted in FIG. 1. The device comprises a first capture area 2 in the form of a chamber with a first inlet 3 through which fluid can flow into the first capture area 2, and a first outlet 4 through which fluid can leave the first capture area 2. The first capture area comprises a plurality of electrodes 5 arranged such that sample will flow over them or come into contact with them when the device is in use. The electrodes 5 are tuned appropriately, as would be understood by one skilled in the art, to trap target cells using DEP when the electrodes are activated. For example in some cases electrodes can use 10 MHz, 5V for *M. Smegmatis*, but actually can work over a whole range of frequencies and voltages depending on flow-rates and electrode geometries.

The device also comprises a second chamber 6, which is both downstream of and in fluid communication with the first capture area 2. There is a second chamber inlet 7 through which fluid can flow into the second chamber 6, and a second chamber outlet 8 through which fluid can leave the second chamber 6. The second chamber comprises a plurality of electrodes 5a arranged such that sample will flow over them or come into contact with them when the device is in use. The electrodes 5a are tuned appropriately, as would be understood by one skilled in the art, to trap target cells using DEP when the electrodes are activated.

In use, a sample is introduced into the first capture area 2 at a first flow rate. The flow rate is regulated by a pump (not shown). The electrodes 5 are activated and as such, target cells (e.g. *M. Tuberculosis* cells or *Mycobacterium smegmatis* cells) in the sample are trapped by DEP forces at least part of the surface of the electrodes 5. The sample continues to flow through the chamber such that target cells continue to be captured whilst the remaining sample eluate from which the target cells have been removed travels to a waste reservoir 9 or other area. After a period of time, which may be a pre-determined period of time, the electrodes 5 are deactivated and the trapped target cells are released from the surface of the electrodes. This results in the media in through the first capture area 2 becoming enriched with target cells (providing, of course, that said target cells were in fact present in the original sample). This is referred to herein as the enriched sample.

The enriched sample is then flowed through a channel, in this example a microfluidic channel, into the second chamber 6. The flow through the second chamber 6 is at a second flow rate that is lower than the flow rate of the sample through the first capture area 2. The electrodes 5a in the second chamber 6 are activated and as such, target cells (e.g. M. Tuberculosis cells or *Mycobacterium smegmatis* cells) in the sample are again trapped by DEP forces at least part of the surface of the electrodes 5a. As the enriched sample will already contain more concentrated volumes of target cells the capture or trapping of the target cells is highly effective.

There is also provided a waste reservoir 9 which could be external to the device in the form of a waste bottle. The first capture area 2 and the second chamber 6 are both in fluid communication with a waste reservoir 9 to allow sample from which the cells have been removed, or unwanted flow through, to be removed. However one skilled in the art would appreciate that this conformation is not essential to the invention.

It would be understood by one skilled in the art that various pre-processing steps and modules can be included prior to the sample being introduced into the first capture area.

It would also be understood by one skilled in the art that various post-processing steps and modules can be included after the target cells are trapped or captured from the enriched sample in the second chamber. For example, the cells could be lysed in situ and then the nucleic acids extracted, enriched or amplified. Also, the electrodes in the second chamber could be deactivated and the target cells released to give a further concentrated sample.

It would be understood by one skilled in the art that whist a first capture area and second chamber are described; additional concentrating chambers could also be included. Whilst the first and second chamber are in fluid communication, other modules, reservoirs and microfluidic structures could be included between the chambers.

Figure 2:
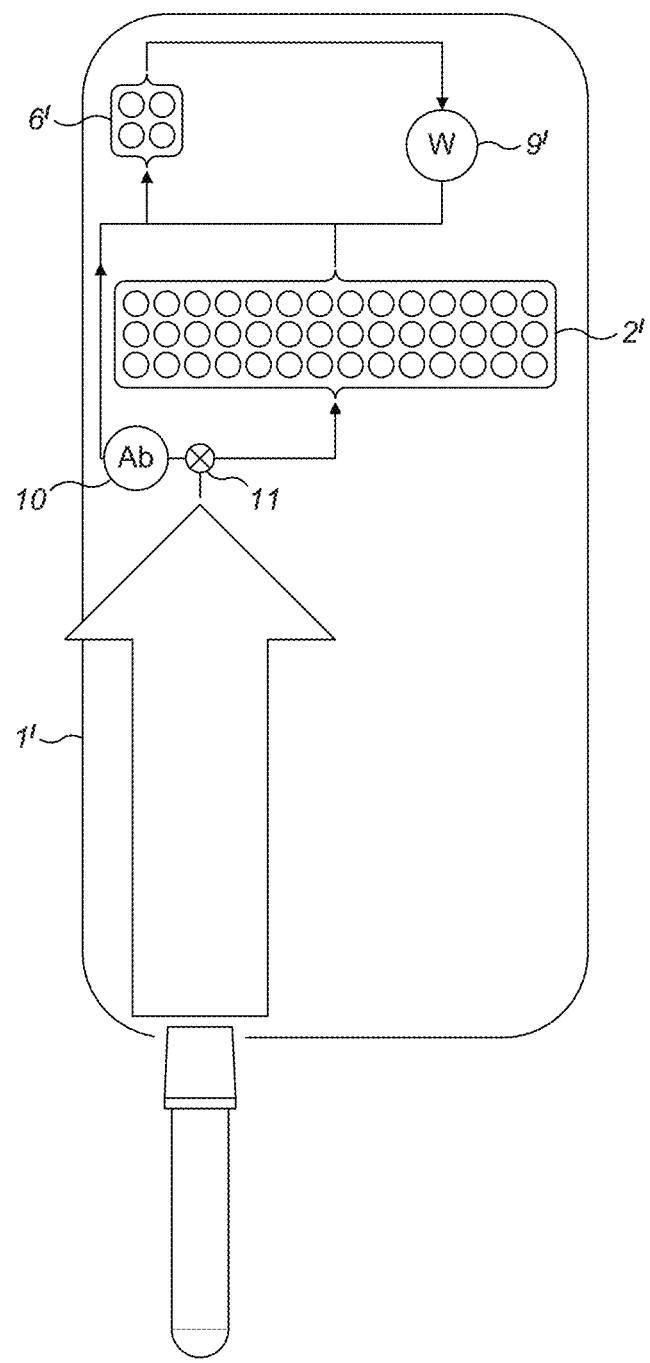
FIG. 2 shows another embodiment of a microfluidic device or portion thereof, in accordance with the present invention.

As best shown in FIG. 2, an antibody reservoir 10 can be included, the antibodies being selected to bind to the cells of interest and either being provided with or being associable with a fluorophore or other marker. One skilled in the art would appreciate that the antibody reservoir 10 could be replaced with a biological dye, stain or other product which would allow identification of target cells during later processing. A system of valves 11 can be used to introduce the antibody into the first capture area 2' or second chamber 6' as required.

The second chamber 6' is provided with either an open top or visually clear upper surface. This is so that, in use, the second chamber 6' can be associated with, or viewed using, an optical detection device (not shown) which is arranged to detect signals from the second chamber. Preferably said optical detection device is capable of detecting, and preferably differentiating or analysing, fluorescence. In this case the optical detection device would comprises an excitation source and a detector.

Figure 4:
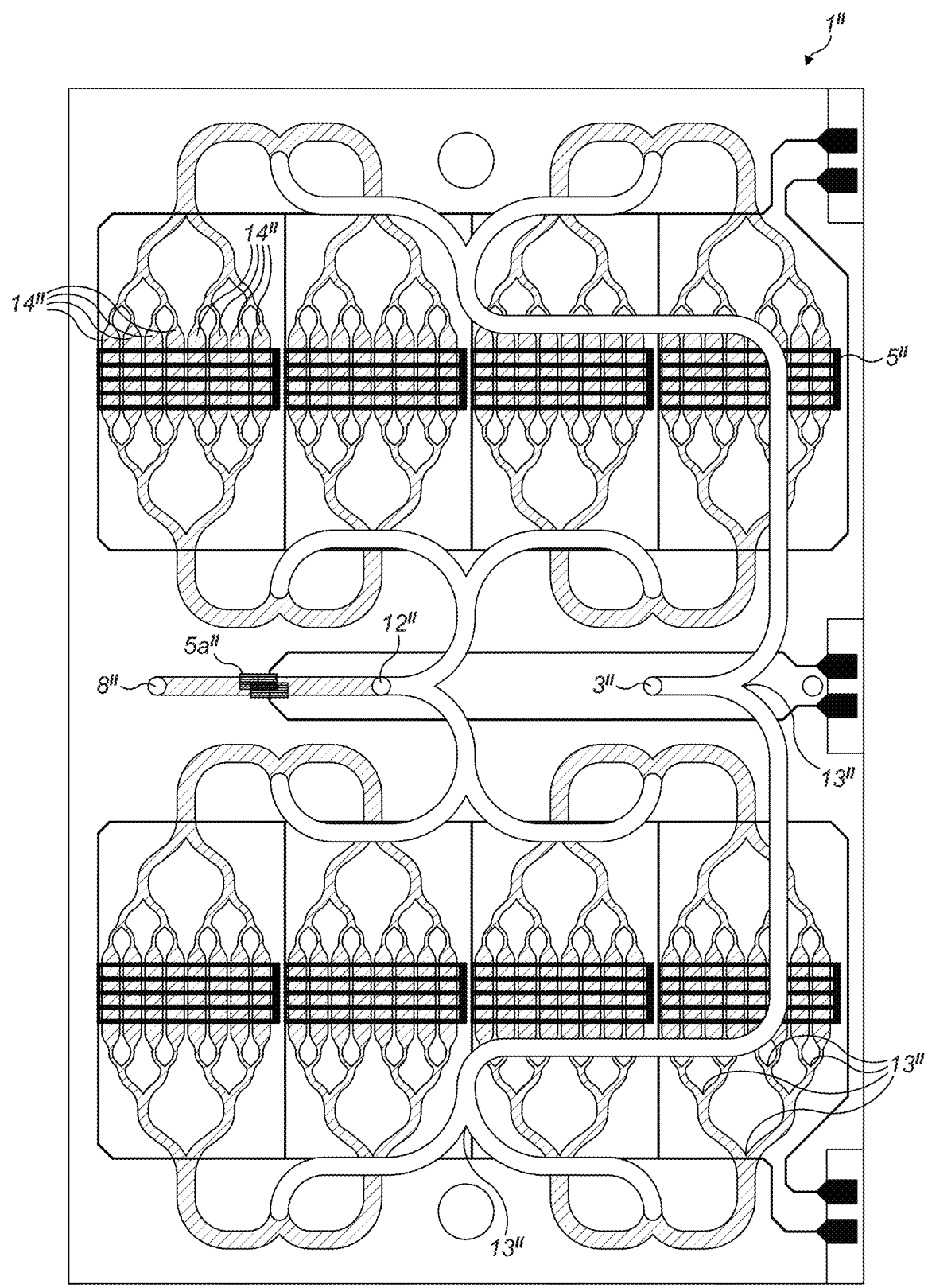
FIG. 4 shows another embodiment of the device with a further variant of the first capture area having bifurcated channels where the design is such that there are in fact multiple first capture areas.

Further, and often preferred embodiments are shown in FIGS. 3 and 4.

In each of these embodiments there is provided a cassette device 1', 1" which has a first capture area 2', 2" positioned upstream from a second capture area 6', 6". The cassette is formed on a glass substrate (although it will be appreciated that other materials could also be used).

In FIG. 3*a*, the first capture area comprises a plurality of electrodes 5' arranged such that sample will flow over them or come into contact with them when the device is in use (as shown more clearly in expanded FIG. 3*b*). The electrodes 5' are tuned appropriately, as would be understood by one skilled in the art, to trap target cells using DEP when the electrodes are activated. For example, in some cases electrodes can use 10 MHz, 5V for *M. Smegmatis*, but actually can work over a whole range of frequencies and voltages depending on flow-rates and electrode geometries.

The first inlet 3' leads into the first capture area. In the embodiment shown in FIG. 3 the channel flowing from the inlet 3' is provided with bifurcations 13', each bifurcated channel is then provided with further bifurcations such that the inlet effectively leads to a plurality parallel channels 14" of smaller circumference than the initial channel. The number of bifurcations can be selected dependent on the required fluid flow. The plurality of parallel channels 14' each flow across the chamber and the electrodes 5' therein. Effectively, in this embodiment, the chamber is in fact a plurality of channels 14' that allow fluid to flow across electrodes, rather than a single open chamber. This allows the fluid flow to be managed. The channels 14' then flow through a reversed version of the bifurcations to ultimately re-join together. Each bifurcation at the inlet end reduces the height, width, or circumference of the channel that leads into it which allows for a large volume sample to be introduced through the inlet 3' and flowed across the first capture area 2' with manageable flow characteristics. Conversely, each bifurcation at the outlet end may increase in height and width, or circumference, compared to the individual channels that lead into it.

Efficient dielectrophoretic immobilization of target sequences required a tuned interaction with the field. Perturbations in flow velocity may alter the response of the target to the field and as such flow velocity must be carefully controlled. To ensure consistent and controlled flow velocity while maintaining high throughput volumes, narrow parallel chambers are required to reduce the effect of varying velocities and possible bubble formation. Within larger channels, flow velocity in the center regions is significantly faster and as such capture cannot be optimized across the device. The use of bifurcation to equally split flow across multiple smaller channels allows greater control of flow velocities for optimized DEP capture.

In the embodiment shown in FIG. 4 the parallel channel concept has been further developed to allow for relatively rapid flow-through of sample in a relatively small footprint. In this embodiment, the substrate is glass and there are a plurality of layers sandwiched together to form the slide or cassette device 1". Providing the substrate as a plurality of layers allows channels to be formed in the layers at different depths that can be particularly useful when engineering the substrate as it allows for easier manufacturing. Some channels can be created at least partially in more than one layer. This can be seen in FIG. 4 where the flow from the inlet 3" is shown as a block white colour and is created in an upper layer which then feeds into channels in a lower layer (indicated in FIG. 4 with parallel lines) at the first bifurcation (in FIG. 4 it should be understood that the first bifurcation does allow fluid flow and the solid line shown in the figure is simply indicative of a change to different layers). The inlet 3" is again configured to have bifurcations 13" splitting the channel into two channels and then further bifurcations result in a plurality of channels 14". The channel that is immediately downstream of the inlet 3" is a relatively deep channel that extends through a plurality of layers of the substrate (or through a layer of the substrate to a depth X), however after the initial bifurcation, further channel bifurcations result in the channels becoming smaller, and these smaller channels are formed in a lesser number of substrate layers (or through a different layer of the substrate to a depth >X), typically in the mid-layer of the substrate.

In this embodiment, the positioning of the channels is such that they do not initially all run parallel but do lead to a plurality of groups of parallel channels 14" of smaller circumference downstream of the inlet 3". Again, the plurality of parallel channels 14" each flow across electrodes therein. Flow can be directed by configuring the channels such that it can flow through multiple first capture areas 2" as shown here. In addition, the device 1" can be multilayered such that the channel depth can be configured easily. A multilayer channel configuration allows for different channels depths leading to the bifurcation zone. It can also allow for a smaller footprint as channels can run in different planes. In this way, pressure is consistently reduced and minimized inside the main capture channels.

The device also comprises a second area 6", which is downstream of and in fluid communication with the first capture area(s) 2" (or chamber(s) 2"). There may be a waste outlet provided between the first area 2" and second area 6" which can be provided with a valve, such that when the valve is in a first position, e.g. open, flow is directed through a waste outlet 12" to a waste chamber or area, and when in a second position, e.g. closed, flow does not exit via the waste outlet and instead is directed to the second area.

There may be a second chamber inlet through which fluid (being the low volume enriched sample) can flow into the second chamber 6" or it may simply be that the second area is positioned downstream and in the fluid flow channel. There may also be a second chamber outlet 8" through which fluid can leave the second area 6". The second area comprises a plurality of electrodes 5a" arranged such that enriched sample will flow over them or come into contact with them when the device is in use. The electrodes 5a are tuned appropriately, as would be understood by one skilled in the art, to trap target cells using DEP when the electrodes are activated.

In use, a sample is introduced into the first capture area 2" at a first flow rate. The flow rate is regulated by a pump (not shown). The electrodes 5" are activated and as such, target cells (e.g. M. Tuberculosis cells or *Mycobacterium smegmatis* cells) in the sample are trapped by DEP forces at least part of the surface of the electrodes 5". The sample continues to flow through the chamber 2" such that target cells continue to be captured whilst the remaining sample eluate from which the target cells have been removed travels via the waste outlet 12" to a waste reservoir or other area. After a period of time, which may be a pre-determined period of time, the electrodes 5" are deactivated and the trapped target cells are released from the surface of the electrodes". This results in the media in the first capture area 2" becoming enriched with target cells (providing, of course, that said target cells were in fact present in the original sample). This is referred to herein as the enriched sample.

The enriched sample does not flow to the waste chamber but instead is then flowed through a channel, in this example a microfluidic channel, into the second chamber or area 6". The flow through the second chamber 6" is at a second flow rate that is lower than the flow rate of the sample through the first capture area 2".

Although the above preferred embodiments describe methods and devices which use electrodes and di-electrophoresis to capture and enrich target cells, it could be envisaged that alternative means for capturing target particles, which are typically cells, could be employed providing they are both selective and able to release any captured particles when required i.e. the binding or capture of cells or particles is reversible. The release could for example use light or chemical changes rather than electrical changes.

It will be appreciated that features from one embodiment may be appropriately incorporated into another embodiment unless technically unfeasible to do so.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A microfluidic device for concentrating target cells, the microfluidic device comprising:
    a first capture area through which a sample can be flowed, the first capture area comprising a plurality of electrodes tuned to trap the target cells using di-electrophoresis (DEP) when activated, and to release the target cells when de-activated, the electrodes arranged such that a sample flowing through the area will flow over them;
    a waste area downstream of the first capture area and in fluid communication with the first capture area;
    a second capture area downstream of the first capture area and in fluid communication with the first area, the second capture area being of a smaller volume than the first capture area and comprising a plurality of electrodes tuned to trap target cells using di-electrophoresis (DEP), the electrodes arranged such that a sample flowing through the second area will flow over them; and
    one or more flow regulators adapted to ensure that the volumetric flow rate of sample travelling through the second capture area is lower than the volumetric flow rate of sample travelling through the first capture area,
    wherein the device is arranged such that, when the electrodes tuned to trap the target cells using di-electrophoresis (DEP) in the first capture area are activated, sample flows out from the first capture area to the waste area, and, when the electrodes tuned to trap the target cells using di-electrophoresis (DEP) in the first capture area are de-activated, sample flows out from the first capture area to the second capture area.

2. The microfluidic device of claim 1, wherein the first capture area is divided into multiple channels.

3. The microfluidic device of claim 1, wherein the device comprises a control module that introduces flow of new buffer or media into the first capture area and/or second area when the electrodes in the first capture area or second area are deactivated.

4. The microfluidic device of claim 1, further comprising an optical detection device.

5. The microfluidic device of claim 4, wherein the optical detection device is arranged to detect signals from the second area.

6. The microfluidic device of claim 1, wherein the waste area is a waste reservoir.

7. The microfluidic device of claim 1, wherein the flow regulators are pumps.

8. A method for concentrating target particles in a sample, the method comprising:
    providing a microfluidic device comprising:
        a first capture area through which a sample can be flowed, the first capture area comprising a plurality of electrodes tuned to trap the target cells using di-electrophoresis (DEP) when activated, and to release the target cells when de-activated, the electrodes arranged such that a sample flowing through the area will flow over them;
        a waste area downstream of the first capture area and in fluid communication with the first capture area;
        a second capture area downstream of the first capture area and in fluid communication with the first area, the second capture area being of a smaller volume than the first capture area and comprising a plurality of electrodes tuned to trap target cells using di-electrophoresis (DEP), the electrodes arranged such that a sample flowing through the second area will flow over them; and
        one or more flow regulators adapted to ensure that the volumetric flow rate of sample travelling through the second capture area is lower than the volumetric flow rate of sample travelling through the first capture area;
    introducing a sample into the first capture area;
    flowing the sample through the first capture area at a first flow rate, with the first plurality of electrodes activated and arranged to trap target particles, and with the sample flow being directed out from the first capture area to the waste area;
    de-activating the first plurality of electrodes and releasing trapped target particles from the first plurality of electrodes to provide an enriched sample;
    directing the enriched sample from the first capture area to the second area; and
    introducing the enriched sample to the second area and flowing the enriched sample through the second area at a second flow rate which is lower than the first flow rate, and with the second plurality of electrodes arranged and activated to trap target particles.

9. The method of claim 8, wherein the releasing trapped target particles from the first plurality of electrodes to provide an enriched sample comprises deactivating the electrodes in the first capture area after a defined period of time to release trapped target particles to provide an enriched sample.

10. The method of claim 8, wherein, prior to releasing the trapped target particles in the first capture area, a new buffer or media is flowed into the first capture area.

11. The method of claim 8, wherein the sample is low salt or low ionic strength.

12. The method of claim 8, further comprising deactivating the electrodes in the second area after a period of time to release trapped target cells to provide a further enriched sample.

13. The method of claim 12, wherein, prior to deactivating the electrodes in the second area a new buffer or media is flowed into the second area.

14. The method of claim 8, wherein an optical detection device is provided, and target particles are viewed using the optical detection device.

15. The method of claim 14, wherein the optical detection device is arranged to detect signals from the second area.

\* \* \* \* \*